United States Patent [19]

Miyata et al.

[11] Patent Number: 4,971,907

[45] Date of Patent: Nov. 20, 1990

[54] METHOD FOR PRODUCING PYRUVIC ACID BY FERMENTATION

[75] Inventors: Reiko Miyata; Tetsu Yonehara; Kyousuke Yotsumoto; Hiromi Tsutsui, all of Aichi, Japan

[73] Assignee: Toray Industries, Tokyo, Japan

[21] Appl. No.: 257,306

[22] PCT Filed: Aug. 21, 1987

[86] PCT No.: PCT/JP87/00621

§ 371 Date: Aug. 18, 1988

§ 102(e) Date: Aug. 18, 1988

[87] PCT Pub. No.: WO89/01523

PCT Pub. Date: Feb. 23, 1989

[51] Int. Cl.$^5$ .......................... C12P 7/40; C12R 1/88
[52] U.S. Cl. ..................................... 435/136; 435/944
[58] Field of Search ................................ 435/136, 944

[56] References Cited

FOREIGN PATENT DOCUMENTS

| 0159492 | 10/1982 | Japan | 435/136 |
| 2275688 | 11/1987 | Japan | 435/136 |
| 3258586 | 10/1988 | Japan | 435/136 |

OTHER PUBLICATIONS

Derwent Abs. 87-060429/09 Noriinsho J62014789 Jan. 1987.

Primary Examiner—Herbert J. Lilling
Attorney, Agent, or Firm—Austin R. Miller

[57] ABSTRACT

By cultivating microorganisms belonging to genus Torulopsis, requiring thiamine and biotin for their growth and having an ability to produce pyruvic acid, it is enabled to accumulate an appreciable amount of pyrivic acid with little by-product.

5 Claims, No Drawings

METHOD FOR PRODUCING PYRUVIC ACID BY FERMENTATION

FIELD OF THE INVENTION

This invention relates to a method for producing pyruvic acid by fermentation.

DESCRIPTION OF THE PRIOR ART

It has heretofore been known to use a microorganism of genus Torulopsis for production of pyruvic acid by fermentation (Journal of Japan Agricultural Chemical Society, Vol. 32, page 573; Japanese Unexamined Patent Publication No.14789/1987).

However, such method is low in accumulation as well as yield of pyruvic acid and is not industrially applicable. According to the Journal of Japan Agricultural Chemical Society Vol. 32, page 573, accumulation of pyruvic acid in use of *Torulopsis candida* is only at 0.5 g/l. Also, according to Japanese Examined Patent Publication No. 14789/1987, accumulation of pyruvic acid in use of *Torulopsis etchellsii* is 5.1 g/l. This *Torulopsis etchellsii* strain has the growth thereof accelerated by the presence of thiamine but does not require thiamine for its growth.

DISCLOSURE OF THE INVENTION

The inventors investigated into a method of producing pyruvic acid which would resolve the foregoing problems and would provide a higher productivity and found that microorganism belonging to genus Torulopsis, requiring thiamine and biotin for the growth thereof and having an ability to produce an appreciable amount of pyruvic acid.

An object of the present invention is to provide a method for producing and accumulating pyruvic acid in a satisfactory rate and yield.

Another object of the present invention is to provide a method for producing and accumulating pyruvic acid with little by-product.

Still another object of the present invention is to provide an improved method using new mutants.

These and other objects of the invention will become more apparent in the detailed description set forth in the following.

These objects are attained by a method for producing pyruvic acid by fermentation which is characterized by culturing a microorganism belonging to the genus Torulopsis, requiring thiamine and biotin for its growth and having an ability to produce pyruvic acid to produce and accumulate pyruvic acid in a culture broth then collecting pyruvic acid from the culture broth.

DESCRIPTION OF THE PREFERRED EMBODIMENTS OF THE INVENTION

The present invention will now be described in detail with reference to some embodiments.

According to the invention, microorganisms belonging to the genus Torulopsis, requiring thiamine and biotin for their growth and having an ability to produce pyruvic acid, are used.

If such characteristics are possessed, microorganisms having other auxotrophic requirements and characteristics such as drug resistance and varying enzyme activity are included in the scope of the invention.

In the invention, there may be used mutants requiring preferably arginine in addition to said requirement for thiamine and biotin for their growth. The auxotrophy for arginine referred to here is of a broad sense and includes the type of incomplete deficiency (or the so-called leaky type) and also the auxotrophy for the biosynthetic precursor of arginine.

Further, in the invention, there may be used mutants having preferably a pyruvate decarboxylase activity (hereinafter referred to as "PDC activity") lower than that of the parent strain in addition to said auxotrophy for thiamine and biotin. Reducing the PDC activity level is likely to serve for less metabolism of pyruvic acid to acetaldehyde, higher rate of conversion from glucose to pyruvic acid and thus greater accumulation of pyruvic acid Also, in the invention, there may be used mutants preferably requiring isoleucine and valine in addition to said requirement for thiamine and biotin for their growth. The isoleucine requirement and valine requirement referred to here are of a broad sense and include the type of incomplete deficiency (or the so-called leaky type) and also the auxotrophy for the biosynthetic precursors of isoleucine and valine.

Further, in the invention, there may be used mutants having a resistance to aminooxyacetic acid in addition to said requirement for thiamine and biotin.

These characters, or auxotrophy, changing enzyme activity and resistance, work effectively for production of pyruvic acid respectively. Thus, microorganisms having some or all of these characteristics are preferably usable.

As microorganisms used according to the present invention, the following may be cited.

(a) *Torulopsis glabrata* TR-2026 (FERM BP-1425)

This TR-2026 strain is a microorganism which requires thiamine, biotin, nicotinic acid and pyridoxine. It had been deposited with the Fermentation Research Institute in Japan as IFO 0005 but was deposited with the Fermentation Research Institute of the Agency of Industrial Science and Technology in Japan (hereinafter referred to as "FRI") on Jul. 31, 1987.

(b) *Torulopsis glabrata* ATCC 32936

This ATCC 32936 strain is a microorganism which requires thiamine, biotin, pyridoxine and nicotinic acid for its growth and has already been deposited with the American Type Culture Center (ATCC) in America.

(c) *Torulopsis methanolovescens* TR 2044
(FERM BP-1428)

This TR-2044 strain is a microorganism which requires thiamine and biotin for its growth. It had previously been deposited with ATCC in America as ATCC 26176 but was deposited with FRI in Japan on Aug. 1, 1987.

(d) *Torulopsis glabrata* X-15 (FERM BP-1428)

This X-15 strain is a microorganism which requires thiamine, biotin, nicotinic acid, pyridoxine and arginine for its growth. It was deposited with FRI in Japan on Apr. 4, 1987.

(e) *Torulopsis glabrata* ACII33 (FERM BP-1424)

This ACII33 strain is a microorganism which requires thiamine, biotin, nicotinic acid and pyridoxine for its growth and has the PDC activity reduced below the parent strain. It was deposited with FRI in Japan on Apr. 4, 1987.

(f) *Torulopsis glabrata* X-68 (FERM BP-1426)

This X-68 strain is a microorganism which requires thiamine, biotin, nicotinic acid, pyridoxine, isoleucine and valine for its growth. It was deposited with FRI in Japan on Jul. 31, 1987.

(g) *Torulopsis glabrata* AOA-8 (FERM BP-1427)

This AOA-8 strain is a microorganism which requires thiamine, biotin, nicotinic acid and pyridoxine for its growth and has a resistance to aminooxyacetic acid, and it was deposited with FRI in Japan on Aug. 1, 1987.

The "FERM BP" numbers are the access numbers of the Fermentation Research Institute in Japan, and the microorganisms having such access number imparted are available for any party requesting them.

These pyruvic acid producing strains (d) to (g) are induced as mutants of, for example, *Torulopsis glabrata* TR2026 as a parent strain.

The mutants are derived relatively with ease by the conventional mutagenic processes. For obtaining a mutant requiring arginine for its growth, the parent strain may be subjected to ultraviolet irradiation or treated with a mutagenic agent (such as, for example, N-methyl-N'-nitro-N-nitrosoguanidine or ethyl methanesulfonate), then the strain growing in a medium containing arginine but not in a medium containing no arginine may be recovered.

To obtain a mutant having a lower PDC activity than the parent strain, the foregoing mutagenic treatment may be made, then the strain of significantly better growth than the parent strain in a medium containing acetic acid may be recovered.

Also, for obtaining a mutant requiring isoleucine and valine for its growth, the foregoing mutagenic treatment is made, then the strain growing in a medium containing both isoleucine and valine but not in a medium lacking either of them may be recovered.

To obtain a mutant having resistance to aminooxyacetic acid, the mutagenic treatment is conducted as above, then the strain growing significantly better than the parent strain in a medium containing aminooxyacetic acid in an amount not sufficient for the parent strain to grow may be recovered.

The PDC activity is determined by breaking the cell by the ultrasonic treatment a, high pressure method using a French press or any other method, then using the supernatant crude enzyme solution by centrifuging, reacting the same with pyruvic acid as a substrate and thiamine pyrophosphate as a supplemental enzyme, then reacting produced acetaldehyde with 2,4-dinitrophenylhydrazine and quantifying 2,4-dinitrophenylhydrazone of acetaldehyde by high performance liquid chromatography.

As strains of lower PDC activities than the parent strains, those having the PDC activity decreased to 70% or less, preferably 60% or less, with the parent strain as a standard, are preferably usable.

Even if strains may not have the PDC activity reduced to 70% or less of the parent strains as a standard, when they have the PDC activity reduced to 70% or less of the wild types from which they are derived, similar effects are attained and so such strains are included in the range of mutants used according to the invention. Here, the PDC activity is expressed in terms of relative activity to the PDC activity of the parent strain as 100%.

The mutants having a resistance to aminooxyacetic acid are those having a stronger resistance than the parent strains or preferably those which, when cultured in a medium containing aminooxyacetic acid in a concentration under which the relative growth rate of the parent strain after 24 hours is 40% or less, show a relative growth rate of 80% or higher. Here, the growth rate is determined by the absorbance at 660 nm of the culture solution and is expressed in terms of the relative absorbance to the absorbonce of the culture solution having no aminooxyacetic acid added of the respective strains as 100%.

According to the present invention any culture media are usable for production of pyruvic acid so long as they adequately contain a carbon source, a nitrogen source, inorganic salts and vitamins etc. For such carbon source, carbohydrates such as glucose, organic acids and alcohols such as ethanol and methanol, which the strain used can utilize, are usable. As the nitrogen source, ammonium sulfate, ammonium nitrate, ammonium chloride, urea, peptone, meat extract, soy bean hydrolyzate and other organic and inorganic nitrogen compounds suffice, but organic nitrogen compounds containing amino acids in good balance are preferable. Inorganic salts include potassium phosphate, magnesium sulfate and other inorganic salts of iron, manganese, etc. Culture medium may further contain the required vitamins such as thiamine, biotin and other vitamins as required, or yeast extract, corn steep liquor and other natural products containing these vitamins.

During culture, the medium has its pH decreased with formation and accumulation of pyruvic acid, and it is effective for production of pyruvic acid to adjust the pH to 3 to 7 with an alkali such as calcium carbonate, caustic soda, caustic potash or ammonia.

The culture temperature is adequately 22° C. to 32° C.

After cultivation, pyruvic acid accumulated in the system can be isolated and recovered by conventional methods. For example, a method of extracting with ether after acidification or of precipitation as phenylhydrazone is usable.

EXAMPLE 1

The fermentation medium (A) shown in Table 6 was introduced in 1l Erlenmeyer flasks, each in 40 ml, and sterilized. Thereafter, separately sterilized calcium carbonate was added for 4%, then *Torulopsis glabrata* TR-2026 (requiring nicotinic acid, pyridoxine, thiamine and biotin for its growth) and *Torulopsis glabrata* ATCC 32936 (requiring nicotinic acid, pyridoxine, thiamine and biotin for its growth) were planted, each in one platinum loop and cultivated at 30° C. for 60 hours independently. After cultivation, pyruvic acid was determined by high performance liquid chromatogtaphy. The results are shown in Table 7. No by-product was detected by high performance liquid chromatography. These culture solutions, collected each in 1l, were centrifuged, then the supernatants had hydrochloric acid added to pH 2.0. They were then extracted with 1l of ethyl ether and adjusted to pH 6.0 with caustic soda and evaporated at 40° C. to 100 ml respectively. With ethanol added dropwise to these concentrated solutions, there were obtained 27.3 g of sodium pyruvate (purity 97%) in the case of the former and 20.1 g of sodium pyruvate (purity 97.3%) in the case of the latter.

EXAMPLE 2

*Torulopsis methanolovescens* TR-2044 (requiring thiamine and biotin for its growth) was planted, in an amount of one platinum loop, to a medium similar to that used in Example 1 except glucose was reduced to 5% and cultivated in a similar method to Example 1. After 60 hours, pyruvic acid in the culture solution was determined by high performance liquid chromatography. The result is shown in Table 7.

EXAMPLE 3

(Separation of L-arginine requiring mutant)

Cells of *Torulopsis glabrata* TR-2026 (requiring nicotinic acid, thiamine, pyridoxine and biotin for its growth) were treated with ethyl methane sulfonate according to a conventional method to induce mutation (hereinafter referred to as "EMS treatment") (1 w/v %, 30° C. for 3 hours) then planted to a nutrient agar medium (GP agar medium [glucose 2.0%; yeast extract 0.2%; polypeptone 5 0%; magnesium sulfate 0 05%; potassium dihydrogen phosphate 0.1%; and agar 2%], product of Daigo Eiyo Kagaku Co.) and cultivated at 30° C. for 2 days to form colonies and, thereafter, each colony was transferred to an agar medium (A) having 5 g/l of ammonium sulfate added to a Bacto Yeast Carbon Base (product of DIFCO Laboratories; hereinafter referred to as "YCB medium") and to an agar medium (B) having 5 g/l of ammonium sulfate and 100 mg/l of L-arginine added to a YCB medium respectively through replica plating. Then, after 3 days of cultivation at 30° C., colonies growing in the agar medium (B) but not in the agar medium (A) according to the method described in Example 4 were isolated by picking to obtain the mutant *Torulopsis glabrata* X-15 requiring L-arginine for its growth.

EXAMPLE 4

(Inspection of arginine requirement)

Strains shown in Table 1 below were cultivated respectively in a slant GP agar medium for 24 hours. For each strain, a very small amount of cells were scraped off and applied in a thin layer to a YCB agar plate medium containing 5 g/l of ammonium sulfate having 0.0% L-arginine added and so that having L-arginine not added and cultivated at 30° C. for 4 days, and the conditions of growth were observed. The strain uncapable of growing in the agar plate cultivation with no addition of L-arginine but growing in the arginine added agar plate medium was taken as a mutant requiring L-arginine for its growth.

The results are as shown in Table 1. *Torulopsis glabrata* X-15 acquires the L-arginine requirement as seen from comparison with the parent strain *Torulopsis glabrata* TR-2026.

TABLE I

| | | (*) Growth L-arginine addition (%) | |
|---|---|---|---|
| | Strains | 0 | 0.01 |
| Parent strain | *Torulopsis glabrata* TR-2026 | + | + |
| Mutant | *Torulopsis glabrata* X-15 | − | + |

Note (*) +: growing; −: not growing

EXAMPLE 5

(Production of pyruvic acid)

40 ml of a fermentation medium (A) shown in Table 6 was introduced in a 1l Erlenmeyer flask, and after sterilization, separately sterilized calcium carbonate was added for 4%, and the arginine requiring mutant *Torulopsis glabrata* X-15 was planted and cultuvated at 30° C. for 60 hours, provided the fermentation medium had 0.01% of L arginine added. The pyruvic acid produced in the culture solution was determined by high performance liquid chromatography.

The results are shown in Table 7.

The method using *Torulopsis glabrata* X-5 had both concentration of accumulation and yield of pyruvic acid appreciably improved over the parent strain.

EXAMPLE 6

(Separation of PDC activity decreased strain)

Cells of *Torulopsis glabrata* TR-2026 (requiring nicotinic acid, thiamine, pyridoxine and biotin for its growth) were treated with EMS according to a conventional method (1 w/v % 30° C. for 3 hours) and then planted in a nutrient agar medium (Gp agar medium, product of Daigo Eiyo Kagaku Co.) and cultivated at 30° C. for 2 days to form colonies and, thereafter each colony was transferred to a basic agar medium (A) comprised of the components shown in Table 6 and the basic agar medium further containing 5 g/l of sodium acetate trihydrate (B) through replica plating. Then, colonies of significantly better growth as cultivated at 30° C. for 3 days in the basic agar medium (B) then in the basic agar medium (A) were isolated by picking. Next, 3 ml of a fermentation medium of the components shown in Table 6 was introduced in 18 mmφ test tubes respectively, and after sterilization, the respective colonies were planted for pyruvic acid fermentation, and accumulations and yields against consumed sugar were examined, and there was obtained a strain, *Torulopsis glabrata* AC II 33, having the yield improved.

EXAMPLE 7

(Determination of PDC activity)

The basic medium shown in Table 6 was introduced in 500 ml shaking flasks, each in 100 ml, and sterilized at 115 for 15 minutes. Then, test strains, *Torulopsis glabrata* TR-2026 and *Torulopsis glabrata* AC II 33 were planted in the medium and cultivated at 30° C. for 30 hours with reciprocal shaking. The cells were harnested from the culture solutions by centifugation and washed twice with 0.2 M potassium phosphate buffer solution of pH 7.2. The washed cells were suspended in 10 ml of the same buffer. After ultrasonic treatment for twenty minutes the homogenate was centrifuged and insoluble components were removed. The supernatant was taken as an enzyme solution.

Preparing a solution of enzyme reaction shown in Table 2, the enzyme reaction was carried out at 30° C. for 20 minutes and the 1 ml of 0.8 mM 2,4-dinitrophenylhydrazine dissolved in 2N hydrochloric acid was added to stop the reaction. The reaction product was allowed to stand for 15 minutes in order to transform the produced acetoaldehyde into its hydrazone. Then adding 2 ml of methanol, 2,4-dinitrophenylhydrazone of acetaldehyde was dissolved and determined by high performance liquid chromatography.

For a control experiment, a reaction solution excluding pyruvic acid was used.

TABLE 2

| Components | Volume |
|---|---|
| 0.18 M aqueous solution of sodium pyruvate | 0.1 ml |
| 2 mM aqueous solution of thiamine pyrophosphate | 0.05 ml |
| 0.05 M citric acid buffer solution (pH 6.0) | 1.25 ml |
| Enzyme solution | 0.1 ml |

The results are shown in Table 3. As shown, the PDC activity of the mutant *Torulopsis glabrata* ACII33 decreased to about ½ of that of the parent strain.

TABLE 3

| Strains | | Relative PDC activities |
|---|---|---|
| Parent strain | *Torulopsis glabrata* TR-2026 | 100 |
| Mutant | *Torulopsis glabrata* ACII33 | 52 |

EXAMPLE 8

A fermentation medium (B) shown in Table 6 was introduced in 1 l Erlenmeyer flasks, each in 40 ml, and sterilized at 115° C. for 15 minutes. Next, 4% of separately sterilized calcium carbonate was added, and one platinum loop of *Torulopsis glabrata* AC 33 was planted and cultivated at 30° C. for 70 hours with rotary shaking. Pyruvic acid produced in the culture solution was determined by high performance liquid chromatography. The results are shown in Table 7.

EXAMPLE 9

(Separation of L isoleucine and L-valine double auxotrophic mutant)

Cell of *Torulopsis glabrata* TR-2026 (requiring nicotinic acid, thiamine, pyridoxine and biotin for its growth) were treated with EMS according to a conventional method (1 w/v %, 30° C. for 3 hours), then planted in a nutrient agar medium (Gp agar medium, product of Daigo Eiyo Kagaku Co.) and cultivated at 30° C. for 2 days to form colonies. Thereafter, they were reproduced by replica plating in an agar medium (I) which had 5 g/l of ammonium sulfate added to Bacto Yeast Carbon Base (product of DIFCO; referred to as YCB medium in the following) and an agar medium (II) which had added to the YCB medium 5 g/l of ammonium sulfate and L-isoleucine and L valine, each in 100 mg/l. Thereafter, cultivating at 30° C. for 3 days, colonies growing in the agar medium (II) but not in the agar medium (I) were isolated by picking. Then, by excluding colonies to be able to grow on a plate medium removed L-isoleucine or L-valine from the agar medium (II). The L-isoleucine and L-valine double auxotropic mutant, *Torulopsis glabrata* X-68 was obtained.

EXAMPLE 10

(Inspection of isoleucine and valine auxotrophy)

Strains shown in Table 4 below were respectively cultivated in a Gp slant medium for 24 hours. Then, each of them was scraped off in a very small amount and applied in a thin layer on a YCB agar medium which had not L-isoleucine and L-valine added and YCB agar medium containing only 0.0% of L-isoleucine, only 0.01% of L valine and both 0.01% of L-isoleucine and L-valine each, then cultivated at 30° C. for 4 days, and the conditions of growth were observed. Then, the mutant unable to grow on the medium of (1) no addition of L-isoleucine and L-valine, (2) addition of only L-isoleucine and (3) addition of only L-valine but able to grow on the agar plate medium containing both L-isoleucine and L-valine was determined as a mutant of L-isoleucine and L-valine double auxotrophy.

The results are shown in Table 4. From comparison with the parent strain, *Tourlopsis glabrata* TR-2026, the L-isoleucine/L-valine double auxotrophic strain, *Torulopsis glabrata* X-68, has obviously acquired a double auxotrophy of L-isoleucine and L-valine.

TABLE 4

| | | Growth condition (*) Addition (%) | | | |
|---|---|---|---|---|---|
| | | 0 | 0.01 (L-Ile) | 0.01 (L-Val) | 0.01 (L-Ile) (L-Val) |
| Parent strain | *Torulopsis glabrata* TR-2026 | + | + | + | + |
| Mutant | *Torulopsis glabrata* X-68 | − | − | − | + |

Note (*) + : Growing −: Not growing
Ile: Isoleucine Val: Valine

EXAMPLE 11

(Production of pyruvic acid)

A fermentation medium (A) shown in Table 6 was introduced in 1 l Erlenmeyer flasks, each in 40 ml. After sterilization, separately 4% of sterilized calcium carbonate was added and the parent strain, *Torulopsis glabrata* TR-2026, and the isoleucine and valine double auxotrophic mutant. *Torulopsis glabrata* X-68, were planted and cultivated at 30° C. for 60 hours. Provided, the mutant was cultivated in the fermentation medium with L-isoleucine and L-valine, each in an amount of 0.01% pyruvic acid produced in the culture solutions was determined by high performance liquid chromatography.

The results are shown in Table 7.

The method using *Torulopsis glabrata* X-68 was appreciably improved over the parent strain in both accumulative concentration and yield of pyruvic acid.

EXAMPLE 12

(Separation of aminooxyacetic acid resistant strain)

Cells of *Torulopsis glabrata* TR-2026 (requiring nicotinic acid, thiamine, pyridoxine and biotin for its growth) were treated with EMS according to a conventional method (1 w/v % 30° C. for 3 hours), then planted in the basic agar medium (A) shown in Table 6 with 8 mM of aminooxyacetic acid added and cultivated at 30° C. for 5 days, and growing large colonies were isolated by picking.

Next, the fermentaton medium (A) shown in Table 6 was introduced in 18 mm$\phi$ test tubes, each in 3 ml. and after sterilization, the colonies were planted, and through pyruvic acid fermentation the pyruvic acid accumulation and its yield against sugar were examined, and a strain having the yield significantly improved, *Torulopsis glabrata* AOA-8 was obtained.

EXAMPLE 13

(Inspection of resistance to aminooxyacetic acid)

Parent strain, *Torulopsis glabrata* TR-2026, and *Torulopsis glabrata* AOA-8 were inoculated in the same amount on the basic medium shown in Table 6 containing aminooxyacetic acid in amounts of 0 mM, 2.5 mM, 5 mM and 8 mM respectively and cultivated at 30° C. for 24 hours to measure the cell growth The results are shown in Table 5. As shown, the growth of *Torulopsis glabrata* AOA-8 was not inhibited on the media containing high concentrations of aminooxyacetic acid as compared with the parent strain and this strain becomes thus an aminooxyacetic acid resistant strain.

TABLE 5

| strains | Relative growth Aminooxyacetic acid addition (mM) | | | |
|---|---|---|---|---|
| | 0 | 2.5 | 5 | 8 |
| Parent strain *Torulopsis glabrata* TR-2026 | 100 | 90 | 2 | 0 |
| Mutant *Torulopsis glabrata* AOA-8 | 100 | 100 | 80 | 71 |

EXAMPLE 14

(Production of pyruvic acid)

The fermentation medium (A) shown in Table 6 was introduced in 1 l Erlenmeyer flasks, each in 40 ml, and after sterilization, 4% of separately sterilized calcium carbonate was added, then the parent strain, *Torulopsis glabrata* TR-2026 and the aminooxyacetic acid resistant strain, *Torulopsis glabrata* AOA-8, were planted, each in one platinum loop, and cultivated at 30° C. for 60 hours. After cultivation, pyruvic acid was determined by high performance liquid chromatography. The results are shown in Table 7.

The method using *Torulposis glabrata* AOA-8 was appreciably improved over the parent strain in both accumulative concentration and yield of pyruvic acid.

TABLE 6

| Components | Basic agar medium (A) | Basic agar medium (B) | Basic medium | Fermentation medium (A) | Fermentation medium (B) |
|---|---|---|---|---|---|
| Glucose | 10 g | 10 g | 10 g | 100 g | 100 g |
| Ammonium sulfate | 5 g | 5 g | 5 g | 1 g | 1 g |
| Na-acetate trihydrate | 0 | 5 g | 0 | 0 | 5 g |
| KH$_2$PO$_4$ | 1 g | 1 g | 1 g | 1 g | 1 g |
| MgSO$_4$.7H$_2$O | 0.5 g | 0.5 g | 0.5 g | 0.5 g | 0.5 g |
| Yeast extract | 0.1 g | 0.5 g | 0.1 g | — | — |
| Pepton | — | — | — | 30 g | 30 g |
| Pyridoxine hydrochloride | — | — | — | 400 μg | 400 μg |
| Nicotinic acid | — | — | — | 2 mg | 2 mg |
| Thiamine hydrochloride | — | — | — | 5 μg | 5 μg |
| Biotin | — | — | — | 5 μg | 5 μg |
| Agar | 20 g | 20 g | — | — | — |
| Total 1 l; Adjusted to pH 5.5 | | | | | |

TABLE 7

| Examples | Strains | Pyruvic acid accumulations (g/l) | Yields against consumed sugar (%) |
|---|---|---|---|
| 1 | *Torulopsis glabrata* TR-2026 | 49.5 | 49.5 |
| 1 | *Torulopsis glabrata* ATCC 32936 | 44.0 | 44.9 |
| 2 | *Torulopsis methanolovescens* TR-2044 | 20.5 | 41.0 |
| 5 | *Torulopsis glabrata* X-15 | 55.8 | 58.0 |
| 8 | *Torulopsis glabrata* ACII33 | 56.8 | 57.9 |
| 11 | *Torulopsis glabrata* X-68 | 53.0 | 55.0 |
| 14 | *Torulopsis glabrata* AOA-8 | 55.0 | 57.1 |

INDUSTRIAL UTILIZABILITY

Pyruvic acid is an important intermediate in metabolism. It is not only a material for synthesis of medicines and pesticides but a main material for synthesis of amino acids such as L-tryptophan, L-cysteine and L-tyrosine by enzymation. Therefore, when produced economically, it was an useful material for synthesis of various compounds.

What is claimed is:

1. A method for producing pyruvic acid by fermentation which is characterized by cultivating microorganisms belonging to genus Torulopsis, requiring both thiamine and biotin for their growth and having an ability to produce pyruvic acid, producing at least 20.5 g/l of pyruvic acid and accumulating pyruvic acid in the culture solution and separating pyruvic acid from said culture solution.

2. A method for producing pyruvic acid by fermentation as set forth in claim 1 wherein the microorganisms require arginine for their growth.

3. A method for producing pyruvic acid by fermentation as set forth in claim 1 wherein the microorganisms have a lower pyruvate decarboxylase activity than the parent strains.

4. A method for producing pyruvic acid by fermentation as set forth in claim 1 wherein the microorganisms require isoleucine and valine for their growth.

5. A method for producing pyruvic acid by fermentation as set forth in claim 1 wherein the microorganisms have resistance to aminooxyacetic acid.

* * * * *

UNITED STATES PATENT AND TRADEMARK OFFICE
CERTIFICATE OF CORRECTION

PATENT NO. : 4,971,907
DATED : November 20, 1990
INVENTOR(S) : Reiko Miyata et al It is certified that error appears in the above-identified patent and that said Letters Patent is hereby corrected as shown below:

Column 2, line 53, delete "1428" and insert therefor --1423--.

Column 3, line 67, delete "80%" and insert therefor --50%--.

Column 5, line 12, delete "5 0%" and insert therefor --5.0%-- and delete "0 05%" and insert therefor --0.05%--.

Column 6, line 38, delete "115" and insert therefor --115°--; and line 51, delete "0.8" and insert therefor --0.5--.

Column 7, line 56, delete "0.0%" and insert therefor --0.1%--.

Signed and Sealed this

Ninth Day of June, 1992

Attest:

DOUGLAS B. COMER

*Attesting Officer*    *Acting Commissioner of Patents and Trademarks*